(12) United States Patent
Johnson (10) Patent No.: US 10,966,474 B2
(45) Date of Patent: Apr. 6, 2021

(54) CALLUS REMOVING GLOVES

(71) Applicant: Mary K Johnson, Charlestown, RI (US)

(72) Inventor: Mary K Johnson, Charlestown, RI (US)

(*) Notice: Subject to any disclaimer, the term of this patent is extended or adjusted under 35 U.S.C. 154(b) by 0 days.

(21) Appl. No.: 16/162,477

(22) Filed: Oct. 17, 2018

(65) Prior Publication Data

US 2020/0121364 A1 Apr. 23, 2020

(51) Int. Cl.
*A41D 19/00* (2006.01)
*A45D 29/00* (2006.01)
*A61B 17/54* (2006.01)

(52) U.S. Cl.
CPC ......... *A41D 19/00* (2013.01); *A41D 19/0006* (2013.01); *A41D 19/0082* (2013.01); *A45D 29/00* (2013.01); *A61B 17/54* (2013.01)

(58) Field of Classification Search
CPC ............... A41D 19/00; A41D 19/0024; A41D 19/0055; A41D 19/01; A41D 19/015; A41D 19/01576; A41D 19/01594; A41D 19/01558; A41D 19/0082; A41D 19/0006; A61B 17/54; A45D 29/00; A45D 29/04; A45D 29/18; A45D 2200/1054; A45D 2029/045
USPC .......................................... 606/131; 451/523
See application file for complete search history.

(56) References Cited

U.S. PATENT DOCUMENTS

| | | | |
|---|---|---|---|
| 3,748,792 A * | 7/1973 | Lamb | A41D 19/01594 451/523 |
| 3,789,555 A * | 2/1974 | Means | B24D 11/001 451/523 |
| 4,038,787 A * | 8/1977 | Bianchi | A41D 19/01594 451/523 |
| 5,082,009 A | 1/1992 | Cromer | |
| D364,226 S | 11/1995 | Hartmann | |
| 5,520,618 A | 5/1996 | Massiet | |
| 5,642,527 A | 7/1997 | Savage | |
| 5,800,446 A * | 9/1998 | Banuchi | A41D 19/0055 2/161.8 |

(Continued)

FOREIGN PATENT DOCUMENTS

GB 2143720 A * 2/1985 ........... B24D 15/045

OTHER PUBLICATIONS

The Sanding Glove. https://www.thesandingglove.com/The-Sanding-Glove.asp (retrieved Jul. 2020); 8 pages including WayBack Machine dates. (2005).*

(Continued)

*Primary Examiner* — Amy Vanatta
(74) *Attorney, Agent, or Firm* — Onofrio Law; Dara L. Onofrio, Esq.

(57) ABSTRACT

A pair of gloves for removing calluses and dry skin including a first glove (11) having an abrasive surface of 100 to 150 grit (7) on at least one finger portion (3) of the glove for removing calluses and dead skin from the heel and other parts of the foot, hand, elbow and knees; and a second glove (12) having an abrasive surface of 200 to 250 grit (8) on at least one finger portion (3) of the glove to remove excess dead skin and to smooth/polish the heel and other parts of the foot, hand, elbow and knees; wherein both gloves have an abrasive surface of 220 to 320 grit on the palm/heel portion (4) of the glove for further polish and smoothing.

10 Claims, 6 Drawing Sheets

(56) References Cited

U.S. PATENT DOCUMENTS

| | | | |
|---|---|---|---|
| D400,714 S | 11/1998 | Chen | |
| 5,885,148 A | 3/1999 | Vargas et al. | |
| D423,225 S | 4/2000 | Chen | |
| 6,557,178 B1 | 5/2003 | Hoover | |
| D476,447 S | 6/2003 | Georgescu | |
| 6,575,822 B2 | 6/2003 | Lowe et al. | |
| D476,920 S | 7/2003 | Price et al. | |
| D479,972 S | 9/2003 | Cueto | |
| D483,910 S | 12/2003 | OBrien, II | |
| D526,180 S | 8/2006 | Holden | |
| 7,093,603 B2 | 8/2006 | Han | |
| D582,097 S | 12/2008 | Hollinger | |
| D604,909 S | 11/2009 | Fierus et al. | |
| 8,062,101 B1 | 11/2011 | Friend | |
| D660,673 S | 5/2012 | Weatherby | |
| D707,526 S | 6/2014 | Daniel | |
| 9,017,149 B2 | 4/2015 | Mauer et al. | |
| D752,812 S | 3/2016 | Sivan | |
| D759,311 S | 6/2016 | Khubani | |
| D765,914 S | 9/2016 | Khubani | |
| D766,508 S | 9/2016 | Wang et al. | |
| 9,434,052 B2 | 9/2016 | Mauer et al. | |
| 2002/0009966 A1 | 1/2002 | Orr | |
| 2004/0016438 A1 | 1/2004 | Han | |
| 2005/0061343 A1 | 3/2005 | Ebner | |
| 2006/0211352 A1* | 9/2006 | Adams | B24D 15/00 |
| | | | 451/523 |
| 2007/0214557 A1 | 9/2007 | Qui | |
| 2007/0244491 A1 | 10/2007 | Russell | |
| 2007/0293130 A1* | 12/2007 | Miekka | B24D 15/02 |
| | | | 451/526 |
| 2009/0293175 A1* | 12/2009 | Cox | A41D 19/0003 |
| | | | 2/161.8 |
| 2015/0289576 A1* | 10/2015 | Woody | A47L 13/18 |
| | | | 2/16 |
| 2016/0113338 A1 | 4/2016 | Cox | |
| 2016/0183978 A1 | 6/2016 | Aniemena | |
| 2016/0262796 A1 | 9/2016 | Coates et al. | |
| 2016/0270820 A1* | 9/2016 | Helton | A61B 17/54 |
| 2017/0049167 A1* | 2/2017 | Champagne | A41D 19/0058 |

OTHER PUBLICATIONS

"Sandpaper" Wikipedia. https://en.wikipedia.org/w/index.php?title=Sandpaper&oldid=805174735 (edition dated Oct. 13, 2017). Retrieved Jul. 2020. 7 pages.*
Silkymit for fee, www.thinkbeauty.com.au, printed Jun. 26, 2017.
Best Callus Removers—Jun. 2017, www.bestgear-guide/best-callus-removers, printed Jun. 26, 2017.

* cited by examiner

CALLUS REMOVING GLOVES

This application claims the benefits of U.S. Provisional application Ser. No. 62/574,066 filed Oct. 18, 2017 which is incorporated herein in its entirety by reference.

FIELD OF THE INVENTION

The present invention relates to callus removing gloves. More specifically, it relates to a glove kit for removing heel and foot calluses.

BACKGROUND OF THE INVENTION

Calluses and hard skin on heels and other parts of the foot, hands, elbows and knees are a common problem for both women and men. Currently available products and services on the market such as foot files/graters, stones, and electronic removers are inadequate due to their inflexibility and inability to follow the natural contour of the foot and/or provide remedy to difficult, inaccessible calluses and hard skin on other parts of the foot such as the ball and toes. Representative patents and publications include U.S. Pat. No. 9,017,149 to Mauer et al.; Des 759,311 to Khubani; Des 364,226 to Hartmann; U.S. 2005/0061343 to Ebner.

Pedicure services provided by nail salons and other establishments utilize these known tools as well as other services such as chemical acid peels. However, these tools and services are not always effective, especially for chronic calluses or people with very dry skin. While the heel may be smooth for a few days, the calluses often return.

Callus knives are another product available but can be dangerous to use and prone to spreading infection if the tools are not cleansed and sterilized properly.

None of the currently available products and services to remove calluses and hard skin on feet is entirely effective for chronic calluses or dry skin. In some individuals their heels are always callused, even after visits to nail salons and/or utilizing tools that are available on the market today.

The main purpose of this invention is to effectively remove tough calluses and dead skin, and smooth/polish the skin on the heel and other parts of the foot. The invention may also be used on other parts of the body such as the hand or elbow to eliminate tough callused skin or just to smooth and polish.

Another purpose of the invention is to provide gloves which are designed to be washable and reusable.

Yet another purpose of the invention is to provide a flexible abrasive surface attached to flexible gloves which allows the user to follow the natural contours of the heel and other parts of the foot.

Another purpose of the invention is to provide better leverage through the use of individual fingers or several fingers together to apply to appropriate levels of pressure to more effectively remove the calluses and hard skin.

Another purpose of the invention is to integrate abrasives on a glove-like device to allow the user to reach small and/or difficult locations of calluses on the foot that foot files, stones and other tools cannot reach, or are ineffective even if they can reach the spot.

Yet another purpose of the invention is to provide a more cost-effective tool to use to remove calluses, as it requires no electricity or battery to operate and it is less expensive than paying for an acid peel at a nail salon.

Another purpose of the invention is to provide a natural solution device and method to remove calluses which avoids the use of harsh chemicals on foot.

Another purpose of the invention device is to provide a better result than known callus remover tools, by creating very smooth heels.

Yet another purpose of the invention is that it is more convenient than having to visit a nail salon since it is designed to be used at home.

Another purpose of the invention is to provide less risk of infection, as it is completely washable.

Another purpose of the invention is that it is reusable, as compared to one-time acid peels.

Yet another purpose of the invention is that it is more likely to be used by men, as they are less likely to visit a nail salon or purchase callus removing products

SUMMARY OF THE INVENTION

In the present invention, these purposes, as well as others which will be apparent, are achieved generally by a pair of gloves for removing calluses and dry skin including a first glove having an abrasive surface of 100 to 150 grid on at least one finger portion of the glove; and a second glove having an abrasive surface of 200 to 250 grid on at least one finger portion of the glove.

In an alternate embodiment, each glove can further include an abrasive surface of 220 to 320 grit which is attached to the heel/palm area of the glove.

The first glove is to remove calluses and dead skin on the heel and other parts of the foot and the second glove is to remove excess dead skin and smooth/polish the heel and other parts of the foot.

The invention gloves can also be used to remove calluses on the opposite hand or other places such as the user's hand, elbow and knee areas.

Each glove preferably has the abrasive surface on four finger portions. In other embodiments the abrasive portion is also on the thumb.

The first and second glove may also include a flexible rubber backing where the abrasive surfaces are adhered to. The rubber backing is adhered directly to the glove surface on the palm side of the glove.

The gloves and abrasive surfaces are flexible and washable. The adhesives used to adhere the materials are also washable and will not disintegrate.

The glove material used is selected from the group consisting of cotton, polyester, a lightweight, cotton/polyester blend, or any washable flexible material.

The invention also provides a glove for removing calluses made of a glove having a finger portion and a palm portion; an opening for the user's hand and at least one abrasive surface on the palm side of the glove surface, wherein the abrasive surface has a grit between 100 to 320.

In this embodiment the abrasive surface is on the finger portions is between 100-150 grit to remove calluses and dead skin from the user's heel and other parts of the foot, hand, elbow or knee.

In an alternate embodiment the abrasive surface is on the finger portions and is between 200-250 grit to remove excess dead skin and smooth/polish the user's heel and other parts of the foot, hand, elbow or knee.

In a preferred embodiment, in addition to the finger portions, an abrasive surface is on said palm portions which have an abrasive surface is between 220-320 grit to further polish and smooth the skin surface.

Also as part of the invention is a method for removing calluses and dry skin comprising the steps of providing a pair of gloves, wherein a first glove has an abrasive surface of 100 to 150 grit on at least one finger portion of the glove;

and a second glove having an abrasive surface of 200 to 250 grit on at least one finger portion of the glove. The user places the first glove on one hand and over the callus and hard skin surface desired to be removed. Using a rubbing motion in a circular and/or back and forth method the abrasive surface removes the calluses or hard skin. After gently brushing off the dead skin, the user places the second glove on their other hand and over the surface where the calluses or hard skin were removed. Using the same rubbing motion in a circular and/or back and forth method the abrasive surface smooths and polishes the area.

In a preferred embodiment both the first and said second glove further include an abrasive surface of 220 to 320 grit on a palm/heel (4) surface to further smooth and polish the area.

Other objects, features and advantages of the present invention will be apparent when the detailed description of the preferred embodiments of the invention are considered with reference to the drawings, which should be construed in an illustrative and not limiting sense.

DETAILED DESCRIPTION OF THE INVENTION

As used herein, the following reference numerals refer to the structures as illustrated in the drawings.
1—opening for the user's hand;
2—abrasive surface;
3—finger portion;
4—palm/heel portion
5—rubber backing (not illustrated but underneath structure 6);
6—abrasive material (mounted on structure 5);
7—100-150 grit abrasive portion;
8—200-250 grit abrasive portion;
9—front side of glove;
10—glove according to the invention
11—Glove 1 (right-handed) for abrasion;
12—Glove 2 (left-handed) for polish;
13—washable abrasive 220-320 grit on palm/heel of hand;
14—finger portion with rounded abrasive (polish);
15—finger portion with rounded abrasive (abrasive); and
16—heel.

Figure 1:
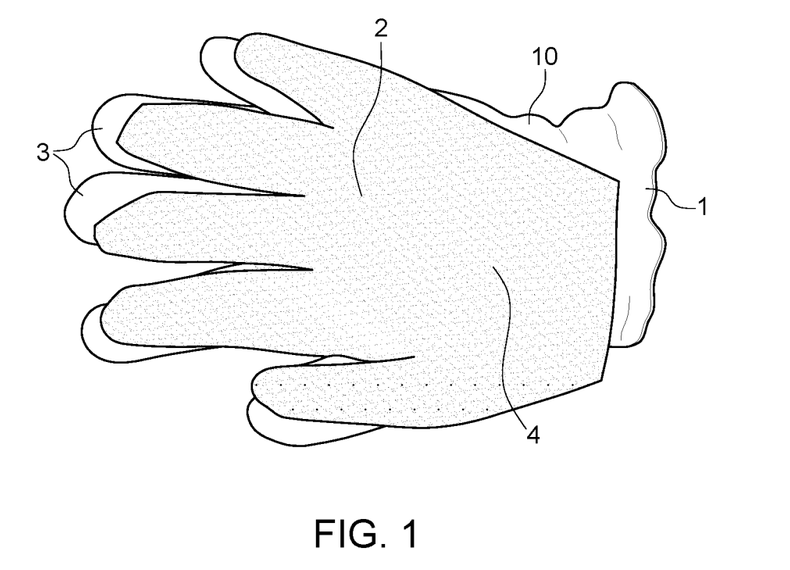
FIG. 1 illustrates the Embodiment 1 of the invention.

As illustrated in FIG. 1 a glove is provided with an entire abrasive surface 2 attached on the underside of the glove 10. The abrasive surface covers the palm portion 4 and the finger portion 3 of the glove. The user slips their hands through opening 1 to place the gloves on. The Embodiment 1 of the invention includes conventional sandpaper and latex gloves. This embodiment is satisfactory in removing calluses and dry skin. However, it is somewhat inflexible and does not provide a smoothing and polishing function.

Figure 2:
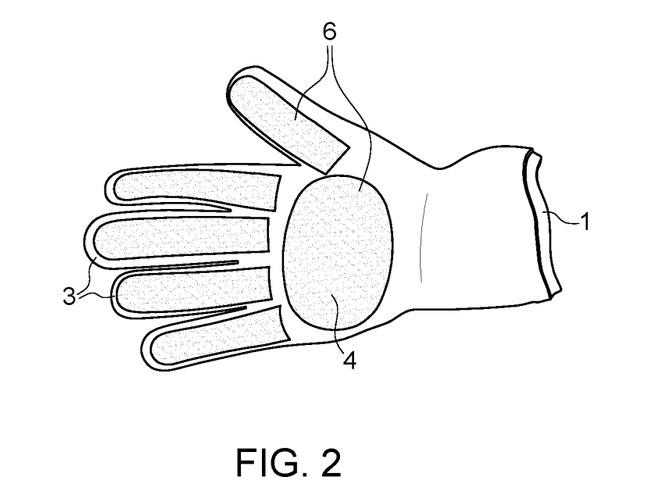
FIG. 2 illustrates the Embodiment 2 of the invention.

Embodiment 2, as shown in FIG. 2, of the invention provides a glove with a flexible rubber backing 5 on the fingers 3 and palm 4 portions of the glove. The abrasive material 6 used in this embodiment is integrated into a flexible rubber-type material. This material used in this embodiment is commercially available and made by 3M company. More specifically, a 150 grit sand paper is attached to the backing on the fingers and a 280 grit sand paper is attached to the backing on the palm. The lower the grit on the sandpaper the heaver the abrasive is. Thus the sand paper on the fingers in embodiment 2 is more abrasive than the sand paper on the palm. The palm sand paper is used for lighter, smoothing and polishing of the skin. The glove material in this embodiment is preferably a cotton/polyester blend glove.

Figure 3:
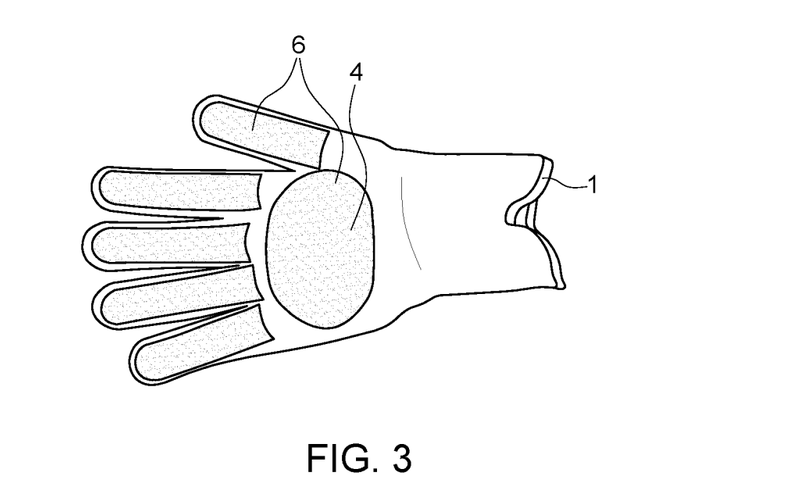
FIG. 3 illustrates the Embodiment 3 of the invention
FIG. 4A, B, C, D illustrates the Embodiment 4 of the invention.

Embodiment 3, as shown in FIG. 3, is similar to embodiment 2 except that different abrasive strips 6 are used as well as a slightly different flexible backing 5 (not illustrated in the drawing since it is underneath the abrasive strips 6). In this embodiment a thinner, flexible abrasive material from a Canadian manufacturer was used. The material was more film like.

Both Embodiments 2 and 3 were tested on removing calluses and dry skin. The results of the testing showed that the single glove combination for removal and polishing was not entirely effective. This testing lead to the development of the glove set of Embodiment 4.

Figure 4A:
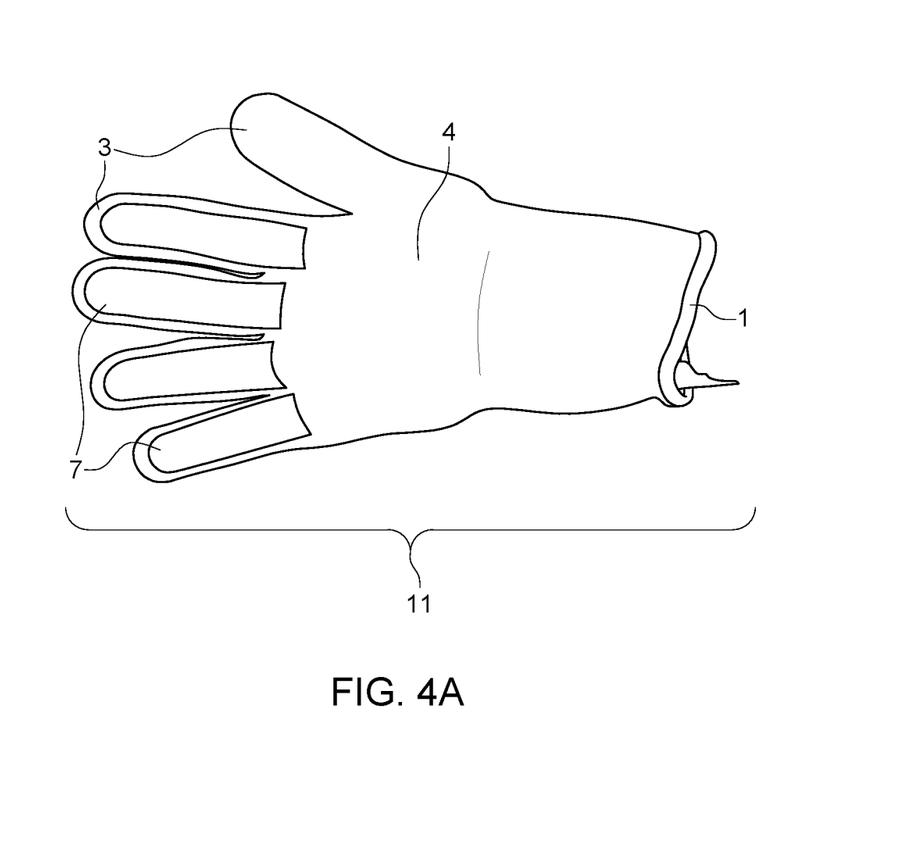

Embodiment 4 of the invention, as illustrated in FIGS. 4A, B, C and D, provides a separate glove for removing the calluses and hard skin and another glove for the smoothing, polishing process.

The glove used in all the embodiments is preferably a cotton/polyester blend. However, other types of fabric such as 100% cotton or all polyester can be used as alternatives. Essentially, the gloves are soft, do not shrink and are easily hand-washed.

Embodiment 4 consists of at least two sanding gloves with two different types of abrasives attached to the four finger areas of the glove, not the thumb or palm. In alternate embodiments, the thumb and the palm can include the abrasive material. See FIGS. 4A, B, C and D. Both gloves, including the abrasives are washable and reusable.

FIG. 4A is an illustration of the first glove—Glove 1 (right-handed) 11 with the 100-150 grit abrasive 7 on the fingers 3. This is the same material as used in Embodiment 3 from 3M. In this embodiment the abrasive 7 is adhered directly to the glove with no rubber backing. On Glove 1, four, ⅝" wide strips of flexible, washable abrasive ranging 100 to 150 grit 7 are attached with a permanent, washable fabric adhesive. The adhesive used was made by Aleen's Original called Fabric Fusion, although any other permanent, washable fabric adhesives can be used. No rubber backing was used in this embodiment, although in an alternate embodiment it is possible to use one.

As depicted in the figures, in this embodiment, there is no abrasive on the thumb. This is so the thumb could be used to support the foot or hand being treated, while removing the calluses or dead skin with the finger portions. However, it is still within the scope of the invention to have abrasive materials on the thumb finger portion.

Length of strips in FIG. 4 are preferably: pointer finger—3 to 4.5 inches; middle finger—3 to 4.5 inches; ring finger—3 to 4.5 inches; pinkie finger—2 to 3.5 inches, although these lengths may be adjusted due to finger and/or glove size. These ranges intend to cover both male and female hands.

Glove 1 11 is the main abrasive tool that is used to remove the hardest, more difficult calluses and dead skin on the heel and other parts of the foot using the rubbing action of all or some of the fingers, as the abrasive used is coarser than Glove 2. As the abrasives are flexible, the user has the freedom to use all or just some of the fingers, and can easily follow the natural contours of the heel and other parts of the foot. In this embodiment there is no abrasive on the palm 4 of the glove.

Figure 4B:
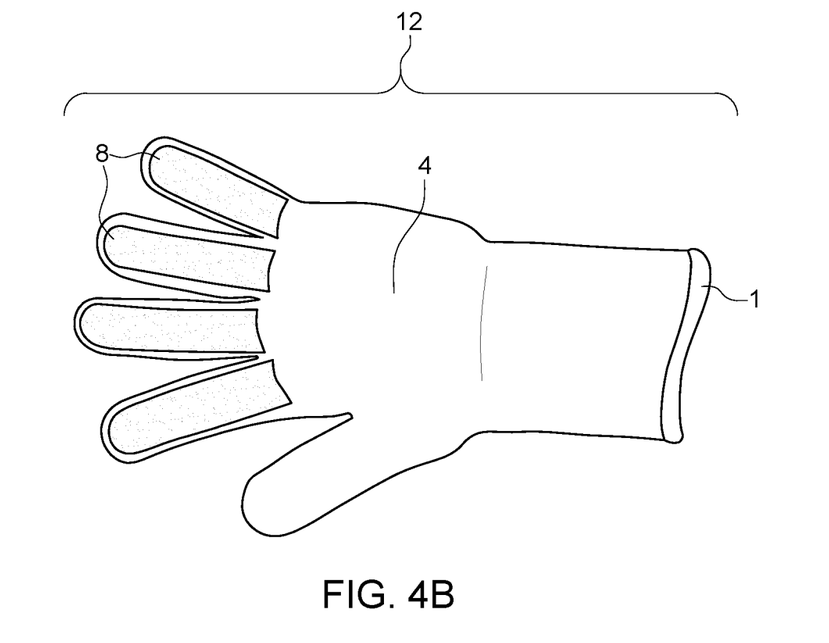

FIG. 4B is an illustration of the second glove—Glove 2 (left-handed) 12. On Glove 2, four, ⅝" wide strips of flexible, washable abrasive ranging from 200-250 grit 8 are attached with a permanent, washable fabric adhesive as described earlier. Length of strips: pointer finger—3 to 4.5 inches; middle finger—3 to 4.5 inches; ring finger—3 to 4.5 inches; pinkie finger—2 to 3.5 inches, although these lengths may be adjusted.

This glove is used to remove excess dead skin and smooth/polish the heel and other parts of the foot. Similarly, the abrasives on the glove are flexible, providing the user the freedom to use all or just some of the fingers, and easily follow the natural contours of the heel and other parts of the foot.

Figure 4C:
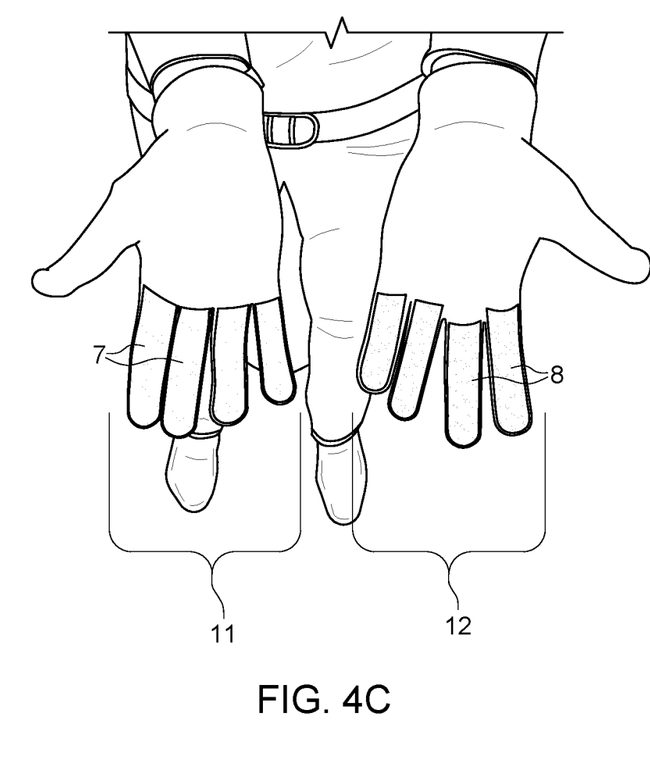

FIG. 4C is an illustration of both Glove 1 11 and Glove 2 12 on the users hand with the respective abrasive sides 7, 8 showing.

Figure 4D:
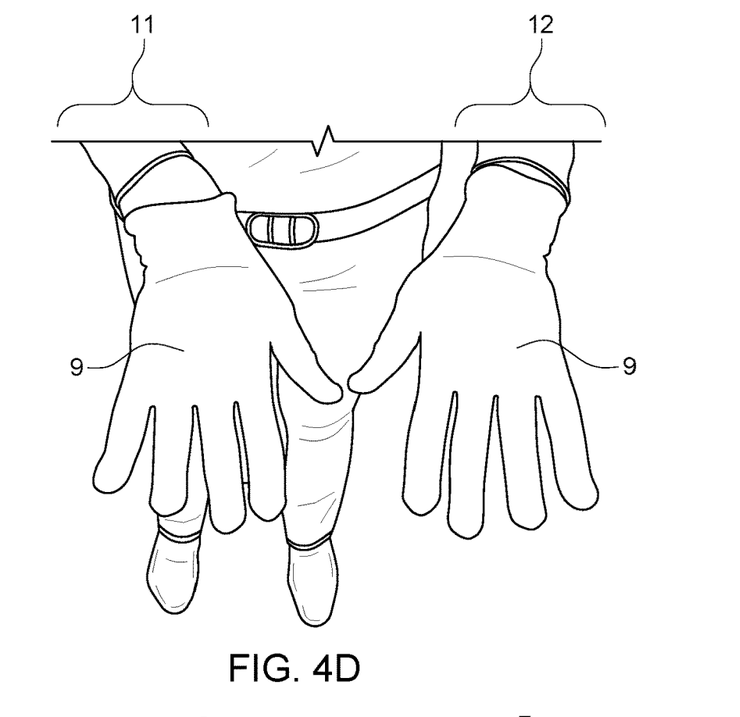

FIG. 4D is an illustration of both Glove 1 and Glove 2 on the user's hand with the back side 9 showing, which has no abrasive on the surface.

In alternate embodiments the abrasives on Glove 1 and 2 can be interchanged for left handed users.

Figure 5:
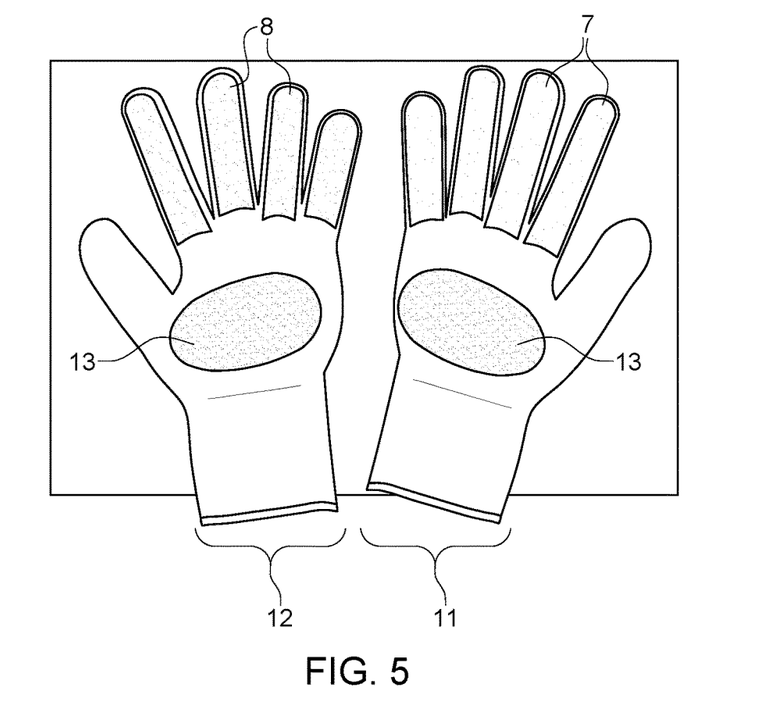
FIG. 5 illustrates the Embodiment 5 of the invention.

Embodiment 5, as illustrated in FIG. 5, contains the same abrasive ranges on the fingers as described in Embodiment 4, but now includes a flexible, washable abrasive ranging from 220 to 320 grit 13 which is attached to both gloves on the heel/palm of the hand to enhance the smoothing/polishing of the heel and other parts of the foot. The abrasive is much finer than that on the fingers of Glove 2 and allows for even better smoothing and polishing. This provides an additional benefit to meet the various preferences of the users and provides a more complete callus removing system.

Figure 6A:
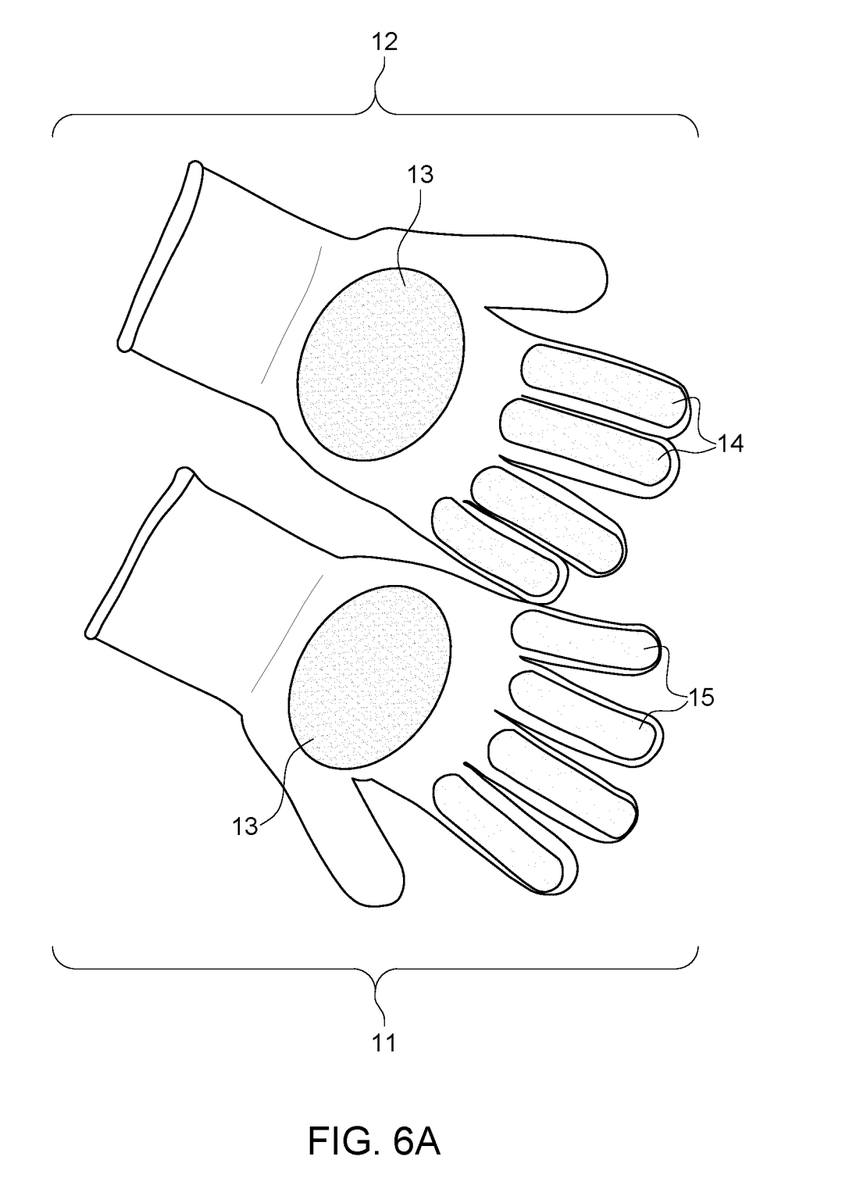
FIGS. 6A and 6B illustrate the Embodiment 6 of the invention.

Embodiment 6, as illustrated in FIG. 6A, is the preferred invention, and contains the same abrasive ranges on the finger portions as described in Embodiment 5 except that the shape of the finger strips are rounded. This allows for better adhesion and more durability to the gloves, although other shapes of the adhesive strips can be used in the invention.

Figure 6B:
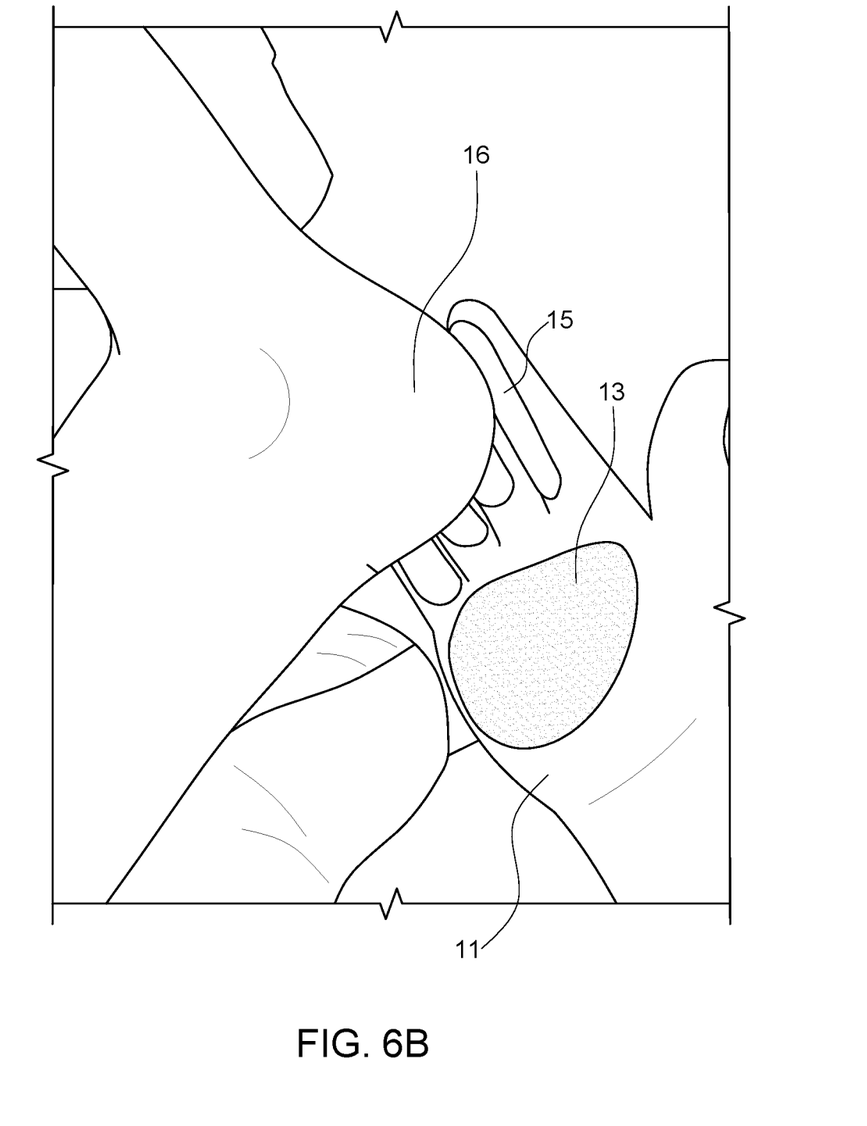

FIG. 6B illustrates use of Glove 1 11 removing calluses on the heel 16 of the user.

The invention devices are used by an individual to remove calluses and dry skin on his or her own body or another person. The user puts on Glove 1 and uses a rubbing action (rubbing motion may include, but is not limited to, back and forth, and circular) to remove the calluses and hard skin off of the heel and other parts of the foot. After gently brushing off the dead skin, the user employs Glove 2 to remove remaining dead skin, and smooth and polish the area. Both gloves can be worn simultaneously, if desired, or one at a time, depending on the user's preference. Again, because the abrasives on the gloves are flexible, the user has the freedom to use all or just some of the fingers, and can easily follow the natural contours of the heel and other parts of the foot.

The preferred glove material used in the invention is a lightweight polyester/cotton blend which is washable. The polyester blend was utilized to reduced potential shrinkage from washing. The glove material can also be all cotton or all polyester. Any glove material that is soft, flexible and washable can be used in the invention.

The permanent adhesive used dries clear, is acid free and is washable. The adhesive used was made by Aleen's Original called Fabric Fusion, although any other permanent, washable fabric adhesives can be used.

A larger version (male version of the invention) may require larger gloves and slightly wider and longer abrasive strips.

Other abrasive materials can be used, particularly for the finishing glove as the film (sanding paper) while washable could be more flexible.

Also other alternatives include adhering the abrasive directly to a glove surface without a flexible backing. In this embodiment the abrasive material would be integrated right into the fabric eliminating the need for a backing and adhesive.

The foregoing description of various and preferred embodiments of the present invention has been provided for purposes of illustration only, and it is understood that numerous modifications, variations and alterations may be made without departing from the scope and spirit of the invention as set forth in the following claims.

What is claimed is:

1. A pair of gloves for removing calluses and dry skin comprising;
    a first glove (11) and a second glove (12) each having a palm-side surface and a top surface wherein each glove is made of a fabric layer having a heel/palm area (13); and four finger portions (3); wherein an abrasive surface is permanently adhered with washable adhesive to select portions of said palm-side surface areas on said heel/palm (13) and said finger portions (3);
    wherein said first glove (11) has an abrasive surface of 100 to 150 grit (7) on said palm-side surface of said finger portions (3) of said first glove;
    wherein said second glove (12) has an abrasive surface of 200 to 250 grit (8) on said palm-side surface of said finger portions (3) of said second glove; and
    wherein said first and second glove has an abrasive surface of 220 to 320 grit on a portion of said heel/palm (13) area.

2. The pair of gloves according to claim 1, wherein a flexible backing is underneath said abrasive surface between said fabric layer and said abrasive surface.

3. The pair of gloves according to claim 1, wherein said first glove is to remove calluses and dead skin on the heel and other parts of the foot, hand, elbow or knee of a user.

4. The pair of gloves according to claim 1, wherein said second glove is to remove excess dead skin and smooth/polish the heel and other parts of the foot, hand, elbow or knee of a user.

5. The pair of gloves according to claim 2, wherein said flexible backing is a flexible rubber backing (5).

6. The pair of gloves according to claim 5, wherein said abrasive surfaces are permanently adhered to said flexible rubber backing (5).

7. The pair of gloves according to claim 1, wherein said abrasive surfaces are permanently adhered directly to said fabric layer.

8. The pair of gloves according to claim 1, wherein said abrasive surfaces are flexible and washable.

9. The pair of gloves according to claim 1, wherein said fabric layer is made of material selected from the group consisting of cotton, polyester, a lightweight, cotton/polyester blend, or any washable flexible material.

10. A method for removing calluses and dry skin comprising the steps of:
    providing a pair of gloves comprising:
    a first glove (11) and a second glove (12) each having a palm-side surface and a top surface wherein each glove is made of a fabric layer having a heel/palm area (13) and four finger portions (3); wherein an abrasive surface is permanently adhered with washable adhesive to select portions of said palm-side surface areas on said heel/palm (13) and said finger portions (3);

wherein said first glove (11) has an abrasive surface of 100 to 150 grit (7) on said palm-side surface of said finger portions (3) of said first glove;

wherein said second glove (12) has an abrasive surface of 200 to 250 grit (8) on said palm-side surface of said finger portions (3) of said second glove; and wherein said first and second glove has an abrasive surface of 220 to 320 grit on a portion of said heel/palm (13) area;

placing the first glove on one hand of a user and over the callus and hard skin surface desired to be removed;

rubbing in a circular and/or back and forth method to remove the calluses or hard skin;

gently brushing off the dead skin;

placing the second glove on the other hand of the user and over the surface where the calluses or hard skin was removed;

rubbing in a circular and/or back and forth method to smooth and polish the area.

\* \* \* \* \*